United States Patent [19]

Frey et al.

[11] 4,148,818

[45] Apr. 10, 1979

[54] PROCESS FOR PREPARING DISILOXANES

[75] Inventors: Volker Frey, Burghausen; Horst Müller, Emmerting; Rudolf Riedle, Burghausen, all of Fed. Rep. of Germany

[73] Assignee: Die Wacker-Chemie GmbH, Munich, Fed. Rep. of Germany

[21] Appl. No.: 927,701

[22] Filed: Jul. 24, 1978

[30] Foreign Application Priority Data

Sep. 15, 1977 [DE] Fed. Rep. of Germany ....... 2741624

[51] Int. Cl.$^2$ .............................................. C07F 7/08
[52] U.S. Cl. ............................................ 260/448.2 E
[58] Field of Search ................................. 260/448.2 E

[56] References Cited

PUBLICATIONS

Noll, "Chemistry and Technology of Silicones", 2nd ed., Academic Press, N.Y. (1968), pp. 42–46.

Primary Examiner—Paul F. Shaver

[57] ABSTRACT

Disiloxanes of the general formula $(CH_2=CHR_2Si)_2O$, where R represents the same or different, monovalent hydrocarbon radicals, are obtained by reacting a compound of the formula $(CH_2=CHRClSi)_2O$ with a Grignard compound of the formula RMgX, where R is the same as above and X represents chlorine, bromine or iodine.

4 Claims, No Drawings

PROCESS FOR PREPARING DISILOXANES

This invention relates to vinyl containing disiloxanes, particularly to divinyltetraorganodisiloxanes and more particularly to a process for preparing the vinyl containing disiloxanes.

BACKGROUND OF INVENTION

The disiloxanes of this invention have been prepared by hydrolyzing the corresponding silanes in accordance with the process described in U.S. Pat. No. 2,716,638 to Cohen et al. In contrast to the process described in the above U.S. patent, the process of this invention utilizes organosilicon compounds which are readily available.

Also, German Patent Application No. 1,118,199 discloses a process for preparing disiloxanes by reacting a dimethylpolysiloxane having a terminal chlorine atom with a Grignard compound having at least three Si-atoms per molecule. Compared to the process described in the German patent application, the process of this invention produces substantially higher yields of vinyl containing disiloxanes.

Therefore, it is an object of this invention to provide a process for preparing vinyl containing disiloxanes. Another object of this invention is to provide a process for preparing vinyl containing disiloxanes from organosilicon compounds which are readily available. Still another object of this invention is to provide a process for preparing vinyl containing disiloxanes in substantially higher yields than have been achieved heretofore. The foregoing objects and others will be apparent from the following description of the invention.

SUMMARY OF INVENTION

This invention relates to a process for preparing disiloxanes of the formula $(CH_2=CHR_2Si)_2O$, which comprises reacting a compound of the formula $(CH_2=CHRClSi)_2O$ with a Grignard compound having the formula RMgX, where R represents the same or different monovelant hydrocarbon radicals, having up to 18 carbon atoms and X is chlorine, bromine or iodine, and thereafter separating the disiloxane from the reaction mixture.

DETAILED DESCRIPTION OF INVENTION

Examples of suitable hydrocarbon radicals represented by R are alkyl radicals, such as the methyl, ethyl, n-propyl, isopropyl, n-butyl and sec-butyl radicals as well as octadecyl radicals; alkenyl radicals, such as the vinyl and allyl radicals; cycloaliphatic saturated hydrocarbon radicals, such as the cyclopentyl and cyclohexyl radicals, as well as the methylcyclohexyl radical; cycloaliphatic hydrocarbon radicals having carbon-carbon multiple bonds, such as cyclohexenyl radical; aryl radicals such as the phenyl radical as well as the xenyl and naphthyl radicals; aralkyl radicals such as the benzyl, beta-phenylethyl and beta-phenylpropyl radicals and alkaryl radicals such as the tolyl radicals.

Methods for preparing compounds of the general formula $(CH_2=CHRClSi)_2O$ are well known. For example these compounds can be prepared from the partial hydrolysis of silanes of the formula $CH_2=CHRSiCl_2$, where R is the same as above or by reacting these silanes with hexamethyldisiloxane.

An example of a preferred compound corresponding to the general formula $(CH_2=CHRClSi)_2O$, which may be used in the process of this invention is 1,3-dichloro-1,3-divinyl-1,3-dimethyldisiloxane.

Grignard compounds and their method of preparation are generally known. Methylchloride and chlorobenzene are preferred examples of compounds having the formula RX, where R and X are the same as above, which may be reacted with magnesium to form the Grignard compound used in accordance with the process of this invention. It is preferred that the Grignard compound used in this invention be prepared in the presence of tetrahydrofuran. Moreover, it is preferred that the tetrahydrofuran be used in excess over the quantity required to form a complex of the Grignard compound.

The process of this invention can be illustrated by the following equation:

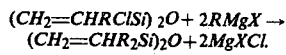

$$(CH_2=CHRClSi)_2O + 2RMgX \rightarrow (CH_2=CHR_2Si)_2O + 2MgXCl.$$

Thus from 2 to 2.3 mols of Grignard compound are preferably used for each mol of disiloxane having Si-bonded chlorine.

In conducting this reaction, it is preferred that the reactants be agitated. In order to facilitate agitation and to increase the yield of product during the recovery of the tetrahydrofuran, it is preferred that the process of this invention be conducted in the presence of at least one solvent which is immiscible with water and which is inert to the reactants and which has a boiling point of at least 100° C. at 760 mm Hg (abs). Examples of such solvents are aliphatic, cycloaliphatic and aromatic hydrocarbons having a boiling point of at least 100° C and more preferably at least 150° C. at 760 mm Hg (abs). Examples of such inert solvents are paraffin oil, turpentine oil, cymene, tetrahydronaphthalene, decahydronaphthalene and dipentene. The inert solvent or a mixture of such solvents can be mixed with the disiloxane and/or with the Grignard compound prior to the reaction or, if only the yield of the tetrahydrofuran is to be increased during its recovery, it can be added to the reaction mixture after the reaction has been completed but, prior to the separation of the desired disiloxane.

The reaction is preferably carried out at −30° C. to 80° C. and more preferably from 20 to 75° C. and at the pressure of the surrounding atmosphere, i.e. at 760 mm Hg (abs) or at approximately this pressure. If desired, lower or higher temperatures and/or pressures may be employed as well.

The desired disiloxane, i.e. a disiloxane having the formula $(CH_2=CHR_2Si)_2O$, where R is the same as above, may be separated from the reaction mixture by any technique known in the art for separating a reaction mixture containing a mixture of organosiloxanes which have been obtained from the Grignard synthesis. If tetrahydrofuran is used, it is preferred that at least 50 percent by weight of the tetrahydrofuran be distilled off prior to the separation of the product from the reaction mixture. This tetrahydrofuran is anhydrous and can be reused in the Grignard synthesis without further purification.

When an inert solvent has been used to aid in the separation of the desired disiloxane the solvent may be reused in a subsequent Grignard synthesis without any futher purification.

The process of this invention provides for very high yields of the desired disiloxane, generally on the order of from 90 to 95 percent of theoretical.

EXAMPLE

A methyl magnesium chloride solution is prepared by adding methylchloride to a mixture consisting of 1000 milliliters of tetrahydrofuran and 97.2 grams (4 mol) of magnesium in the form of magnesium shavings until the shavings have dissolved. About 400 grams (1.76 mol) of 1,3-dichloro-1,3-divinyl-1,3-dimethyldisiloxane is added dropwise to the methyl magnesium chloride solution with constant agitation and at a temperature between 25 and 75° C. About 1000 milliliters of paraffin oil having a boiling point of about 190° C. at 760 mm Hg (abs), is added, then about 700 milliliters of anhydrous tetrahydrofuran is distilled off until a bath temperature of 150° C. is obtained. The residue obtained from this distillation is mixed with 70 milliliters of water. About 280 milliliters of tetrahydrofuran having a water content of less than 0.5 percent by weight is recovered. After cooling, the residue obtained from the second distillation is mixed with 600 milliliters of water and 100 milliliters of 20 percent aqueous hydrochloric acid and from the organic phase is obtained 317 grams i.e. 94 percent of theoretical, of 1,3-divinyl-1,1,3,3-tetramethyldisiloxane having a boiling point of from 138 to 139° C. and a purity in excess of 98 percent by weight.

What is claimed is:

1. A process for preparing disiloxanes of the formula $(CH_2=CHR_2Si)_2O$, which comprises reacting a compound of the formula $(CH_2=CHRClSi)_2O$ with a Grignard compound of the formula RMgX, where R is a monovalent hydrocarbon radical and X is selected from the class consisting of chlorine, bromine and iodine and thereafter recovering the disiloxane from the reaction medium.

2. The process of claim 1, wherein the reaction is conducted in the presence of an inert solvent which is immiscible in water.

3. The process of claim 1, wherein an inert solvent which is immiscible in water is added after the reaction has been completed and prior to recovering the disiloxane from the reaction medium.

4. The process of claim 1, wherein X is chlorine.

* * * * *